United States Patent [19]

Garofalo

[11] 4,074,373

[45] Feb. 21, 1978

[54] SYSTEM FOR ATTACHING PILLOW TO X-RAY TABLE

[75] Inventor: Frank S. Garofalo, Old Westbury, N.Y.

[73] Assignee: F. Garofalo Electric Co., Inc., Brooklyn, N.Y.

[21] Appl. No.: 656,006

[22] Filed: Feb. 6, 1976

[51] Int. Cl.² .............................................. A47C 21/00
[52] U.S. Cl. ......................................... 5/325; 5/317 R
[58] Field of Search ............... 128/133, 134; 269/128; 297/219, 284, 391, 397; 24/265 R, 115 K; 5/325, 322, 338, 92

[56] References Cited

U.S. PATENT DOCUMENTS

| | | | |
|---|---|---|---|
| 2,986,202 | 5/1961 | Yates | 5/325 X |
| 3,220,767 | 11/1965 | Hendickson | 297/219 |
| 3,279,849 | 10/1966 | Radke et al. | 297/DIG. 6 |
| 3,313,511 | 4/1967 | Koerner et al. | 297/DIG. 6 |
| 3,578,383 | 5/1971 | Earl | 297/391 |
| 3,779,540 | 12/1973 | Boudreau | 5/317 R |
| 3,783,863 | 1/1974 | Kliever | 269/328 |
| 3,867,046 | 2/1975 | Fox | 24/115 K |

Primary Examiner—Peter M. Caun
Attorney, Agent, or Firm—Roy C. Hopgood; John M. Calimafde; Charles W. Neill

[57] ABSTRACT

This invention is a system for attaching pillows to an X-ray table or the like. A belt is connected with the pillow by construction that permits pillow-slips to be replaced for each patient without disturbing the permanent connection of the belt to the underside of the pillow. The belt extends to opposite sides of the X-ray table, where it can be looped around belt holders so as to bring end portions of the belt into position overlying the parts of the belt between the pillow and the belt holders. Detachable fastening means on the confronting surfaces of the overlying portions of the belt can be pressed together to hold the end portions of the belt in their looped positions about the belt holders and to maintain the pillow in a center position on the table.

10 Claims, 5 Drawing Figures

U.S. Patent  Feb. 21, 1978  4,074,373
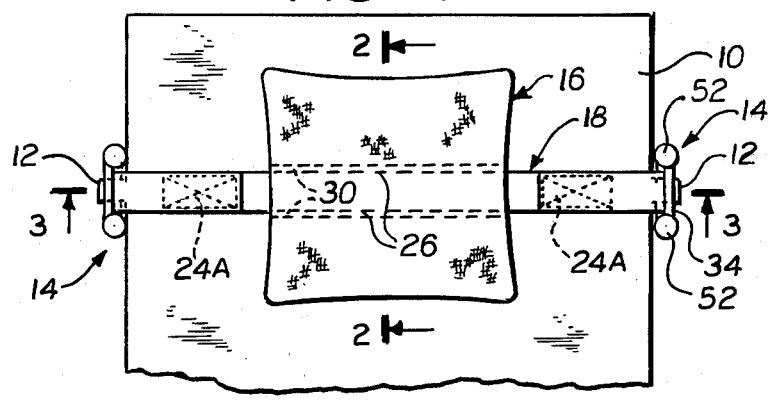
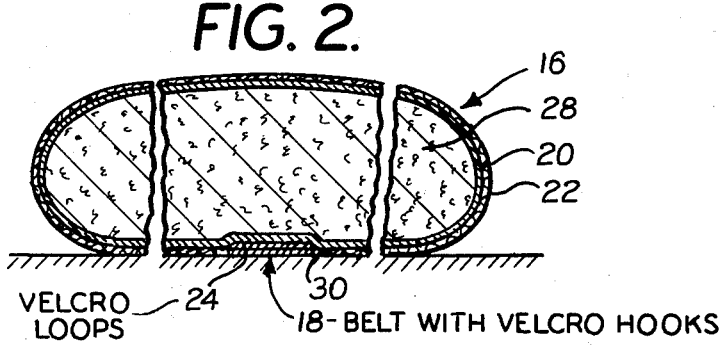
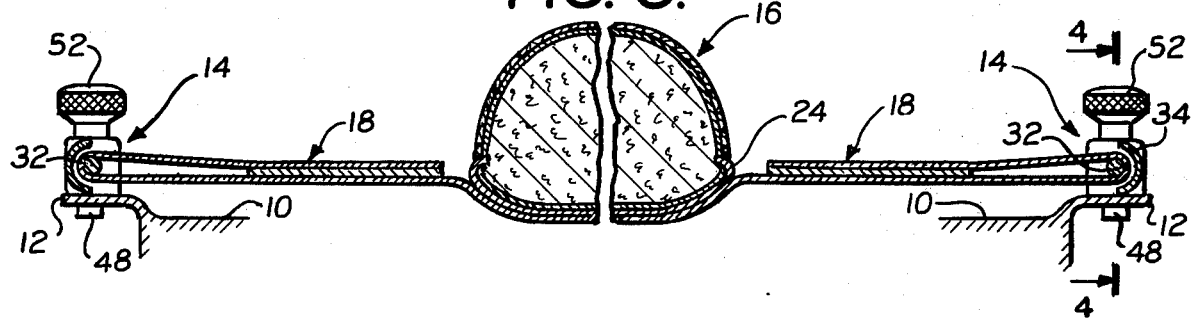
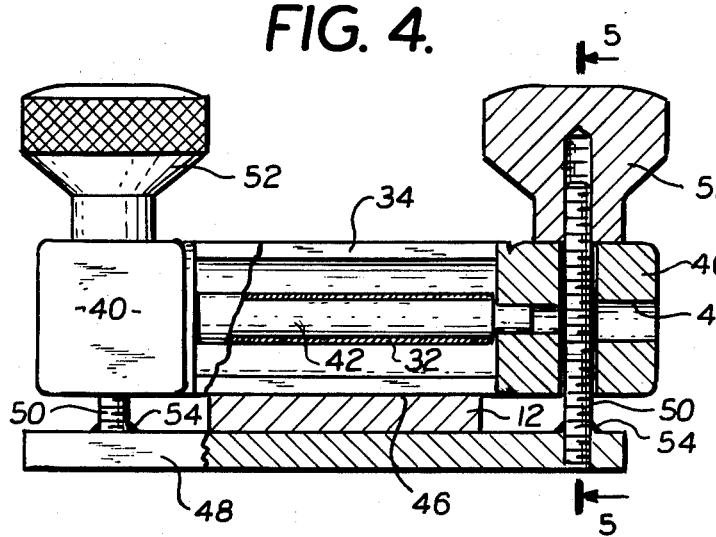
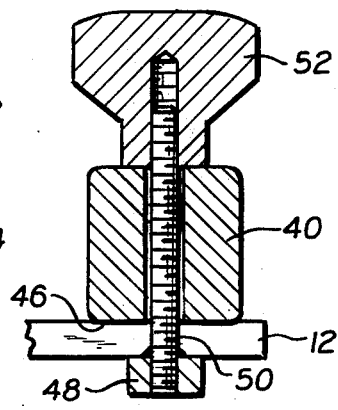

SYSTEM FOR ATTACHING PILLOW TO X-RAY TABLE

BACKGROUND AND SUMMARY OF THE INVENTION

There are times when pillows are desirable on X-ray, treating tables and the like, such as tables used by osteopaths for treating patients; and it is desirable to have means for holding the pillow in place on the table while still permitting quick and convenient removal of the pillow and its holding means when not necessary.

This invention provides a system for holding a pillow centered on an X-ray table, or the like, by means of a belt which is permanently attached to the pillow and which is looped through belt holders at opposite sides of the table for holding the pillow in a centered position.

The belt holders, which are preferably clamps that connect with the table along its opposite edges, have surfaces around which end portions of the belt can be looped back over those parts of the belt which extend between the pillow and the belt holders. The loops can be pulled tight and adjusted with respect to one another to center the pillow on the table.

The confronting faces of the looped end portions of the belt have detachable fastening means of their contacting surfaces. Such detachable fastening means are used on various pieces of medical equipment where quick and convenient connection and disconnection is desirable. The most common form consists of rows of extremely small plastic hooks extending from one surface, and a complementary surface with loops into which the hooks engage to hold the surfaces together. When sufficient force is applied to pull them apart, the hooks are flexible enough to bend outwardly into substantially straight shapes so that they slip out of the loops on the confronting surface.

Features of the invention relate to the construction of the belt holders for convenient clamping and unclamping with respect to the table on which they are used; and to means for guiding the ends of the belt around the surfaces over which the belt reverses its direction of extent and loops back on itself. The belt is permanently attached to the pillow in the preferred embodiment of the invention; but a pillow-slip that is used on the pillow, and that is changed for each patient, is constructed with a clearance that permits the pillowcase to be removed and replaced while leaving the belt and pillow permanently connected together.

Other objects, features and advantages of the invention will appear or be pointed out as the description proceeds.

BRIEF DESCRIPTION OF DRAWING

In the drawing, forming a part hereof, in which like references characters indicate corresponding parts in all the views:

FIG. 1 is a top plan view showing a portion of an X-ray table or the like with a pillow held in place by the retaining system of this invention;

FIG. 2 is a greatly enlarged sectional view taken on the line 2—2 of FIG. 1;

FIG. 3 is a greatly enlarged, fragmentary, sectional view taken on the line 3—3 of FIG. 1;

FIG. 4 is an enlarged view partly in elevation and partly in section along the line 4—4 of FIG. 3; and FIG. 5 is a sectional view taken on the line 5—5 of FIG. 4.

DESCRIPTION OF PREFERRED EMBODIMENT

FIG. 1 shows an X-ray table 10 with tabs 12 extending from the opposite edges thereof, and belt holders 14 clamped to the tabs 12.

A pillow 16 is permanently attached to a belt 18 which extends across the table 10 and through the belt holders 14 for holding the pillow in a center position between the opposite edges of the table 10.

FIG. 2 shows the pillow 16 with stuffing 20 enclosed in a covering 22. Across the bottom of the pillow there is a band 24 of soft material comprising a multitude of loops. The belt 18 is preferably made with a multitude of hooks extending from its upper surface throughout the entire length of the belt. Such loops and hooks are well-known expedients for connecting surfaces together and are sold under the tradename "Velcro." They are used in the preferred embodiment of this invention, but may be considered representative of detachable fastening means by which surfaces of contiguous objects can be held in contact with one another.

The pillow 16 is thus detachably connected with the belt 18 along a band indicated by the dotted lines 26 in FIG. 1. Referring again to FIG. 2, there is a pillowcase 28 on the pillow 16. This pillowcase 28 has a panel which covers the entire top surface of the pillow 16 and all of the bottom surface except for an elongated opening 30 in the pillowcase which provides clearance for the belt 18. The length of the slot 30 is clearly shown in FIG. 1, and with this slot it is possible to easily and quickly remove the pillowcase 28 without detaching the pillow 16 from the belt 18.

FIG. 3 shows the belt 18 extending from opposite sides of the pillow 16 and looping around surfaces in the belt holders 14. With the belt holders 18 clamped to the tabs 12 of the table 10, the belt 18 is connected with the belt holders by leading each end of the belt under a shaft 32 and into contact with a surface of a connecting element 34 of the belt holder. This connecting element 34 has a face of generally cylindrical contour spaced from the circumference of the shaft 32 with sufficient clearance to permit the end of the belt to pass along the concave surface of the connector element 34. As the end of the belt is advanced along this concave surface, the end portion of the belt forms a loop which is then pulled toward the pillow 16 until the loop is tight against the shaft 32, as shown in FIG. 3.

The end portions of the belt 18 have material providing loops 24A, similar to those on the pillow 16 for engaging the hooks on the surface of the belt between the pillow 16 and the belt holder 24 after the belt loop has been pulled tight, as in FIG. 3. For more economical manufacture, the belt 18 has hooks extending along its entire length; but the loop section 24A is applied over the hooks and permanently secured in place on the belt by stitching it to the belt.

The construction of both end portions of the belt is the same, and since the portion of the belt between the pillow and the belt holders always has hook areas under the end portion which has been looped back from the belt holders, the looped belt at both sides of the pillow can be secured with both loops tight to hold the pillow centered on the table and regardless of whether the length of belt beyond each side of the pillow is the same as that beyond the other side. It may be said that the end portion of the looped belt can be secured to the confronting face of the other portion of the belt at an infinite number of locations, as a result of the use of the Velcro fastening means.

FIGS. 4 and 5 show the belt holders in more detail. The connecting element 34 is attached at its opposite ends with blocks 40 and as a unitary structure with the blocks 40. The blocks 40 and connector 34 can be of one-piece construction, if desired, or they can be rigidly connected to one another to provide the unitary structure. In the construction illustrated in FIG. 4, the shaft 32 is hollow, and a rod 42 extends through the shaft 32 and provides a bearing surface on which the hollow shaft 32 can rotate freely. This facilitates the looping of the belt around the shaft 32 and also facilitates the removal of the belt from the belt holders.

The rod 42 extends into openings 44 in the blocks 40. The diameter of the openings 44 where the rod 42 enters these openings is preferably of a diameter to make the rod a press fit in the blocks 40.

The blocks 44 and connecting element 34, particularly the connecting element, comprise an upper clamping jaw 46 of the belt holder. There is a lower clamping jaw 48, and the tabs 12 of the table are clamped between these jaws, as shown in FIGS. 4 and 5. There are screws 50 connected with the lower clamping jaw 48 and extending upward through vertical openings in the blocks 40. The screws 50 extend above the upper ends of the blocks 40, and there are knobs 52 threaded over the upper ends of the screws 50. The screws 50 move up and down, to close and open the clamping jaws, depending on the direction of rotation of the knobs 52.

In the construction illustrated, the screws 50 are rigidly connected with the lower clamping jaw 48 and prevented from turning with respect to the clamping jaw by welding 54 or other securing of the lower ends of the screws 50 to the clamping jaw 48. The screws 50 could, of course, be secured to the knobs 52 and thread through the lower clamping jaw 48, this being merely a reversal of parts.

The preferred embodiment of the invention has been illustrated and described, but changes and modifications can be made and some features can be used in different combinations without departing from the invention as defined in the claims.

What is claimed is:

1. A system for attaching a pillow to an X-ray table or the like, including, in combination, a belt for connection with a pillow with which the system is intended to be used, belt holders for opposite sides of the table, one of the belt holders including means for detachably securing it to one edge of the table and having a surface extending generally transverse of the length of the belt and around which the belt is looped to change the direction in which the belt extends around an angle of approximately 180°, whereby an end portion of the belt extends along a part of the belt between the pillow and the belt holder, and detachable fastening means that connect the end portion of the belt with said part of the belt over which the end portion extends after being looped around said surface of the belt holder, and characterized by a concave guide with which an end of the belt contacts to lead the end portion of the belt into a loop around said surface of the clamp, the concave guide being a connecting element of generally cylindrical contour and extending for the full length of said surface, the belt holder having a block secured to each end of the connecting element and integral therewith, and a shaft extending between the blocks and having a circumferential surface that constitutes the surface about which the belt is looped.

2. The system described in claim 1 characterized by the shaft being rotatable with respect to the blocks, and bearings supporting the opposite ends of the shaft from the respective blocks for providing the rotation of the shaft.

3. The system described in claim 1 characterized by the shaft being hollow and being supported by a rod, the rod providing the bearing on which the shaft is rotatable, and the rod extending into the blocks at its opposite ends and of unitary construction with the blocks to provide an additional connection between the blocks in addition to the connecting element of generally cylindrical contour.

4. The system described in claim 1 characterized by the belt holder being a clamp with the blocks and the parts which are integral with the blocks forming one jaw of the clamp, a second jaw of the clamp movable with respect to the blocks and other integral parts connected with the blocks, screws extending through the respective blocks and connected at their lower ends with the movable clamping jaw, and manually-operated knobs at the upper ends of the respective blocks and into which the screws extend for bringing the clamping jaws together or moving them apart by rotating the knobs one way or the other.

5. The system described in claim 1 characterized by said detachable fastening means including complementary surfaces that contact with one another, each of said surfaces including elements that adhere to the other surface when the surfaces are brought into contact with one another, and that pull loose from one another when subjected to more tension than they encounter when the belt is being used under the working conditions in which it is intended to be used.

6. The system described in claim 5 characterized by the complementary surfaces including rows of small plastic hooks projecting from an area of one surface of the belt and a multitude of loops on the other surface of the belt and with which the hooks engage.

7. The system described in claim 1 characterized by a pillow attached to the belt and in contact with the top surface of the belt, the belt beyond the pillow extending under the surfaces about which the end portions of the belts are looped, and each end portion of the belt extending across the top of the portions of the belt between the pillow and the belt holders.

8. The system described in claim 7 characterized by a pillowcase on the pillow, said pillowcase having an upper panel for contact with a patient lying on the table, and the pillowcase having a lower panel with an open area providing clearance for the portion of the belt that extends under the pillow, whereby the pillowcase can be changed for each successive patient while the belt remains permanently connected with the pillow on the underside thereof.

9. The system described in claim 1 characterized by a pillow attached to a mid-portion of the top surface of the belt, the connection of the pillow to the belt being detachable and comprising a looped surface and a surface with rows of small plastic hooks that confront one another to provide detachable connection of the pillow to the belt.

10. The system described in claim 9 characterized by the loop area being attached to the bottom of the pillow and the rows of hooks projecting from the top surface of the belt, the belt having a similar surface with rows of hooks projecting therefrom throughout the entire length of the belt, but the end portions of the belt which are to be connected to other parts of the belt after the belt is looped having a layer of loop material overlying the hooks and secured to the belt by permanent fastening structure.

* * * * *